United States Patent [19]

Vaughn et al.

[11] Patent Number: 5,006,267

[45] Date of Patent: Apr. 9, 1991

[54] BIOCIDAL FLUID FILTERS

[75] Inventors: Walter L. Vaughn, Lake Jackson; Thomas J. McKeand, Jr., Clute; Robert T. Patton, Lake Jackson, all of Tex.

[73] Assignee: The Dow Chemical Company, Midland, Mich.

[21] Appl. No.: 433,488

[22] Filed: Nov. 8, 1989

[51] Int. Cl.$^5$ .............................................. C02F 1/50
[52] U.S. Cl. ..................................... 210/755; 55/279; 55/524; 210/764; 210/501; 210/504; 210/508; 422/38; 422/122; 514/642
[58] Field of Search ................. 55/279, 524; 210/755, 210/764, 209, 501, 504, 505, 506–508, 510.1, 638, 500.1, 500.35; 422/28, 37, 122; 514/642, 643

[56] References Cited

U.S. PATENT DOCUMENTS

| 3,328,367 | 6/1967 | Rees | 260/85.5 |
|---|---|---|---|
| 3,471,460 | 10/1969 | Rees | 260/88.1 |
| 3,872,128 | 3/1975 | Byck | 260/286 R |
| 4,601,831 | 7/1986 | Cook | 210/501 |
| 4,615,937 | 10/1986 | Bouchette | 428/288 |
| 4,621,120 | 11/1986 | Hollister | 514/642 |
| 4,661,634 | 4/1987 | Vaughn et al. | 564/292 |
| 4,802,997 | 2/1989 | Fox et al. | 252/173 |
| 4,837,079 | 6/1989 | Quantrille et al. | 428/288 |
| 4,876,070 | 10/1989 | Tsukahara et al. | 210/501 |

OTHER PUBLICATIONS

"Antimicrobial Polymers"—Ackart et al.—J. Biomed. Mater. Res.—vol. 9—pp. 55–68 (1975).

Primary Examiner—Peter Hruskoci

[57] ABSTRACT

A water insoluble material useful for making biocidal barriers and biocidal filter for use in fluid systems, said material comprising a water insoluble thermoplastic copolymer consisting of an alpha olefin and an alpha, beta-ethylenically unsaturated carboxylic acid, said copolymer having at least one biocidal agent ionically bonded to said copolymer.

23 Claims, No Drawings

BIOCIDAL FLUID FILTERS

FIELD OF THE INVENTION

The present invention relates to novel biocidal filters for use in fluid systems. More particularly, there is provided a filter comprising a water insoluble thermoplastic copolymer having a cationic biocidal agent ionically bonded therewith in particle or fiber form having biocidal activity in connection with fluid systems.

BACKGROUND OF THE INVENTION

There is a need for sanitizing fluid streams which are either liquid or gaseous. Sanitation of facilities by a kill-on-contact mechanism rather than by introducing chemicals can be beneficial for both the environment and the user. Addition of chlorine or other chemicals at times is not convenient or desirable. Further chlorination of swimming pools or whirlpools in spas can cause eye and skin irritations. Hot tubs are not commonly chlorinated. However, such facilities at times require means for controlling bacterial or fungal growth.

There are many antimicrobial preparations for suppressing mold, mildew and odor-causing bacteria. Such preparations include solid biocide concentrates as described in U.S. Pat. No. 4,086,297. The commercial preparation of Morton Thiokol, Inc. sold under the trademark VINYZENE is an additive to plastics which comprises 10, 10'-oxybisphenozas that is active against a broad spectrum of fungi and bacteria. The product is in the form of a 2 weight percent solution in mineral spirits or methyl ethyl ketone and as a 5 weight percent blend in a thermoplastic resin. These products are used as biocides in the field of wood preservatives, swimming pools, food preservatives, sanitizers and disinfectants, industrial water treatment and plastics. However, none of the prior art biocides are reacted with the substrate on which they are utilized.

None of the prior art means have provided a method for treatment of systems such as air conditioners or vents which may disperse in air fungus or bacteria. Such air ladened microorganisms are believed to have caused illnesses and respiratory ailments.

Biocides which are commercially available include active halogens, for example chlorine, chlorinated isocyanurates, halophors and the like, phenolics, quaternary ammonium salts including alkylbenzyl-dimethylammonium chloride, where the alkyl group contains 12-18 carbon atoms and dimethyldialkylammonium chloride, where the alkyl group contains 8-10 carbon atoms.

U.S. Pat. No. 3,328,367 to Rees, discloses ionic copolymers which can be utilized as coatings or in laminates.

U.S. Pat. No. 3,471,460 to Rees discloses diamine modified hydrocarbon copolymers comprising a copolymer of an alpha-olefin and an alpha, beta-ethylenically unsaturated carboxylic acid which are useful as films and coatings. None of the Rees patents are concerned with biocidal copolymers or hydrogels.

U.S. Pat. No. 3,437,718 and U.S. Pat. No. 3,970,626, which are herewith incorporated by reference disclose suitable methods for preparing the precursor copolymers which are used in the present invention.

U.S. Pat. No. 4,661,634 to Vaughn et al, which is herein incorporated by reference, discloses the use of ionomers for removing impurities from quaternary ammonium salts.

The particles and fibers which comprises an alpha-olefin copolymerized with an olefinically-unsaturated carboxylic acid forms a "quat acrylate copolymer" when combined with quaternary ammonium salts.

Application serial No. 157,202 filed Feb. 17, 1988 of Patton et al entitled, "Polymer Salt Complex for Fiber or Fabric Treatment", which is herein incorporated by reference, discloses fabrics coated with copolymers of alpha olefins and alpha, beta-ethylenically unsaturated carboxylic acids that are modified with quaternary ammonium salts.

It is understood that the term "particles" as used herein relates to powders, platelets, pellets, and the like.

SUMMARY OF THE INVENTION

The present invention provides a biocidal filter for use in fluid systems comprising a water insoluble biocidal thermoplastic copolymer of an alpha-olefin and an alpha, beta-ethylenically-unsaturated carboxylic acid, said copolymer having at least one biocidal agent ionically bonded thereto.

As used herein the expression "biocidal filters" is used to encompass materials and structures useful as permeable biocidal barriers which utilize the biocidal properties of the material, yet which might not be all considered as "filters" in the ordinary sense of the word. For instance, permeable sheets, membranes, "curtains", dividers, or wrappings made of the biocidal material permit the passage of fluids through the structure in either of both directions, and because of the biocidal activity of the material, are actually barriers to the passage of live microbes.

Advantageously, the biocidal copolymer is a hydrogel and in fiber or particle form. Preferably the biocidal groups are uniformly distributed throughout the copolymer. Generally, when the copolymer is not a hydrogel the biocidal groups are found only on the surface of the copolymer. Utilizing microporous or cellular copolymers provides a greater surface area to contact the microorganisms and to carry the biocidal agent. However, hydrogels carry a greater amount of the biocidal agents.

More particularly, there is provided filter elements comprising particles or fibers of an ionomer or copolymer of an alpha-olefin having the general formula R—CH=CH$_2$, where R is selected from the group consisting of hydrogen and alkyl radicals having from 1 to 8 carbon atoms, and an alpha, beta-ethylenically unsaturated carboxylic acid having up to 12 carbon atoms, which has been modified by a reaction with biocidal agent capable of being ionically bonded therewith. In accordance with a preferred embodiment of the invention the copolymer is in the form of a hydrogel. The acid monomer content of the copolymer is about 5 to 50% mole, preferably 15 to 25% based on the copolymer.

The cationic biocidal agents which are capable of being ionically bonded with the copolymers of the invention to form the biocidal particles and fibers include monoalkyltrimethyl ammonium salts such as cetyltrimethyl ammonium bromide (CTAB), alkyltrimethyl ammonium chloride (commercial available as ARQUAD 16), monoalkyldimethyl benzyl ammonium salts which are commercially available as BTC 824, HYAMINE 3500, and RISEPTIN (dodecyldimethyl-3,4-dichlorobenzyl ammonium chloride), dialkyldimethyl ammonium salts, heteroaromatic ammonium salts such as cetylpyridium halide, alkylisoquinolinium bromide, bis-quaternary salts such as 1,10-bis (2-methyl-4-aminoquinolinium chloride)-decane, polymeric quaternary ammonium salts such as poly[oxyethylene (dimethylimino) ethylene (dimethyliminio)-ethylenedichloride], 2-(4-thiozolyl) benzimidazole, N[alpha(1-nitroethyl)benzyl) ethylenediamine, 6-chloro-9[4-diethylamino-1-methylbutyl amino]-2-methoxy acridine dihydrochloride, and the like.

The preferred biocidal agents used in modifying the copolymer and ionomer of the invention is selected from the group consisting of alkylbenzyldimethyldialkylammonium halide, wherein the alkyl group contains 8–10 carbon atoms. Advantageously, the biocidal agent forms about 30–50% by weight of the reaction product.

The biocidal agent modified copolymers and ionomers of the invention can be prepared by reacting an ionomer or copolymer with a suitable biocide by milling, melt blending, slurrying the polymer with a solution of the biocidal agent of the invention or by passing an alkaline solution of the biocidal agent through a fabricated article of the ionomer or copolymer. Preferably, the ionomer or copolymer is made into a hydrogel and then treated with the biocidal agent.

The biocidal copolymers of the invention may be used alone or blended with other inorganic or polymeric fibers or particles which are inert in the system they are utilized.

Suitable polymeric fibers or particles which may be blended include polyolefins, for example, polyethylene, polypropylene, and the like, polyvinyl chloride, polyvinyl acetate, polyvinylidene chloride, and the like.

The copolymer or ionomer may be blended with other thermoplastic materials prior to reaction with the biocidal agent to provide a fiber or particle characteristic for use in a specific environment.

The biocidal materials of the invention may be in various forms, for example, fibers, fibrous mats, fibrous woven or non-woven fabrics, fibrous cartridges or canisters, porous membranes, sintered particles, hollow fibers, powders, pellets, and the like.

The invention provides antimicrobially active filter elements in fiber or particle form which may be used alone or with fillers in fluid systems, for example, for water purification and sanitization, control of yeast formation in fermentation reactions, control of fungus and mold in air conditioning systems, reduction of air borne microorganisms in sterile environments such as operating rooms, control of microorganisms in brackish water, etc. However, the biocidal copolymers are most effective at a pH of 6 to 8. Generally, leaching of the biocidal agent occurs at a pH below about 4.

DESCRIPTION OF THE PREFERRED EMBODIMENTS

In accordance with the present invention a copolymer comprised of an alpha-olefin and an alpha, beta-ethylenically-unsaturated carboxylic acid or an ionomer of said copolymer is reacted with a cationic biocidal agent capable of forming an ionic bond therewith. In accordance with a preferred embodiment of the invention the biocidal agent is a quaternary ammonium salt selected from the group consisting of alkylbenzyldimethylammonium halide, wherein the alkyl group contains 12 to 18 carbon atoms and dimethyldialkylammonium halide, wherein the alkyl group contains 8 to 10 carbon atoms. Most preferable of the quaternary ammonium salts is dimethyldidecyl ammonium chloride.

Example of suitable olefins include ethylene, propylene, butene-1, pentene-1, hexene-1, heptene-1, 3-methylbutene, pentene-1, and the like.

Examples of suitable acid monomers include acrylic acid, methacrylic acid, ethacrylic acid, itaconic acid, maleic acid, fumaric acid, and maleic anhydide. Maleic anhydride is not a carboxylic acid, however, it can be considered an acid for the purpose of the invention because its reactivity is that of an acid. Similarly other monoethylenically unsaturated anhydrides of carboxylic acid can be used.

The copolymer base need not necessarily comprise a two component polymer. More than one olefin can be employed to provide the hydrocarbon nature of the copolymer base. Other copolymerizable monoethylenically unsaturated monomers, illustrative members of which are mentioned below in this paragraph, can be employed in combination with the olefin and the carboxylic acid comonomer. The scope of base copolymers suitable for use in the present invention is illustrated by the following examples: ethylene/acrylic acid copolymers, ethylene/methacrylic acid copolymers, ethylene/itaconic acid copolymers, ethylene/methyl hydrogen maleate copolymers, ethylene/maleic acid copolymers, ethylene/acrylic acid/methyl methacrylate copolymers, ethylene/methacrylic acid/ethylacrylate copolymers, ethylene/itaconic acid/methyl methacrylate copolymers, ethylene/methyl hydrogen maleate/ethyl acrylate copolymers, ethylene/methacrylic acid/ vinyl acetate copolymers, ethylene/acrylic acid, ethylene/acrylic acid/vinyl alcohol copolymers, ethylene/acrylic acid/carbon monoxide copolymers, ethylene/propylene/acrylic acid copolymers, ethylene/methacrylic acid/acrylonitrile copolymers, ethylene/fumaric acid/vinyl methyl ether copolymers, ethylene/vinyl chloride/acrylic acid copolymers, ethylene/vinylidene chloride/acrylic acid copolymers, ethylene/vinylidene chloride/acrylic acid copolymers, ethylene/vinyl fluoride/methacrylic acid copolymers, and ethylene/chlorotrifluoroethylene/methacrylic acid copolymers.

The copolymers may also, after polymerization but prior to ionic crosslinking, be further modified by various reactions to result in polymer modifications which do not interfere with the ionic crosslinking. Halogenation of an olefin acid copolymer is an example of such polymer modification.

The preferred base copolymers, however, are those obtained by the direct copolymerization of ethylene with a monocarboxylic acid comonomer. Such copolymers as hydrogels provide unexpected advantages.

The ionic copolymers are obtained by the reaction of the copolymer with an ionizable metal compound which is well known and referred to as neutralization. As such, the ionomers have at least 5 percent by weight, preferably from about 20 to about 100 percent by weight, of the acid groups neutralized. Metal ions which are suitable for neutralizing the copolymers of the present invention are selected from monovalent, divalent and trivalent metals of Groups I, II, IV-A, and VIII of the Periodic Table of Elements. Specific examples of suitable monovalent metal ions are selected from $Na^+$, $K^+$, $Li^+$, $Cs^+$, $Rb^+$, $Hg^+$, and $Cu^+$. Examples of suitable divalent ions include $Be^{+2}$, $Mg^{+2}$, $Ca^{+2}$, $Sr^{+2}$, $Ba^{+2}$, $Cu^{+2}$, $Cd^{+2}$, $Hg^+$, $Sn^{+2}$, $Pb^{+2}$, $Fe^{+2}$, $Co^{+2}$, $Ni^{+2}$, and $Zn^{+2}$. Trivalent metal ions suitable for use herein are selected from the group of $Al^{+3}$, $Sc^{+3}$, $Fe^{+3}$, and $Y^{+3}$.

The preferred metals suitable for neutralizing the copolymers used herein are the alkali metals of Group I, particularly cations such as sodium, lithium, potassium, and alkaline earth metals of Group II, in particular, cations such as calcium, magnesium, and zinc. It should be noted that more than one metal ion may be incorporated into the copolymer in certain applications.

A convenient method of preparing the ionomers herein is disclosed in U.S. Pat. No. 3,437,718, issued to Rees, entitled Polymer Blends. In particular, the metal compound is added to an alpha-olefin/alpha, beta-ethylenically unsaturated carboxylic acid and the mixture is milled at a temperature of from about 140° to about 180° C. for about 15 minutes or until the reaction proceeds to completion. The disclosure of U.S. Pat. No. 3,437,718 is incorporated herein by reference.

Another method of preparing the alkali metal salts of copolymers herein is disclosed in U.S. Pat. No. 3,970,626, issued to Hurst et al, on July 20, 1976; the disclosure of which is incorporated herein by reference. In particular, the reference teaches a hydrolysis process for preparing aqueous copolymer salt emulsions of alpha-olefin, alpha, beta-ethylenically unsaturated carboxylic acids by suspending a particular alpha-olefin, alpha beta-ethylenically unsaturated carboxylic acid ester interpolymer in water having an alkali metal dissolved therein and heating said mixture to a temperature of at least 180° C. under autogenous pressure for a period of time sufficient to enable the alkali metal to react with a sufficient portion of the ester groups of the copolymer to render said copolymer emulsifiable in the aqueous alkali medium.

According to the present invention the copolymer or ionomer is first formed into the pertinent structure, that is, fiber, mat, felt, particles, etc. The copolymer or ionomer is then ionically bonded with a cationic biocidal agent, which is preferably a quaternary ammonium salt. The reaction which takes place is a replacement reaction wherein the metal group of the ionic polymer is displaced by the biocidal agent. Preferably, the copolymer is reacted with a base so as to form a hydrogel and then the quaternary ammonium compound and/or other biocidal agent is ionically bonded to the copolymer. With a hydrogel there is a greater distribution of the biocidal agent throughout the copolymer so as to provide better efficacy.

Briefly, the biocidal hydrogel materials may be prepared as follows:

A fabricated article is swollen/digested with hot (50°-70° C.) aqueous base (such as 2.0 wt. % sodium hydroxide) to form a hydrogel, then the excess caustic is rinsed away with deionized water the swollen/digested polymer is treated with an aqueous solution containing the cationic biocidal agent (for example, a quaternary salt) and the biocidal agent is ionically bonded (interchanged for sodium which is released into the solution).

The biocidal polymer is thoroughly washed with deionized water to remove any labile or unreacted salts. The necessity of this step depends on the intended uses of the product.

Alternatively, ethylene-acrylic acid copolymers (or an equivalent) is extruded (85°-88° C.) into a strand alone or blended with another thermoplastic with some orientation (including "cold-drawing" the strand at a temperature below that at which stress relaxation can occur) prior to chopping the strand into strand chopped pellets. The pellets are swollen for 2–5 hours in 2.0 wt. % sodium hydroxide aqueous solution at a temperature of 50°–65° C. to induce conversion to the ethylene-sodium acrylate hydrogel (ion exchange thermoplastic pellet). The caustic is drained, the pellets are washed with deionized water and hammered into fiber using a hammermill. The resulting fiber are water washed and sized by pumping an aqueous slurry of the hammered fiber through screens of different mesh. Generally it is desirable to separate the fibers of 50 mesh and smaller from those of a coarser size. The coarse fiber (18–50 mesh) are suitable for s while the fine fiber (>50 mesh) is suitable for shallow beds and use as an additive. The water washed fiber (pH 8–11) is contacted with an aqueous stream containing the biocidal agent and the biocidal agent ionically bonds to the fiber. The biocidal agent which is a quaternary ammonium salt is chemically bound to the copolymer as a quaternary acrylate compound.

Residual biocidal agents (if any) are washed from the fiber with deionized water along with sodium salts.

The filters of the invention can comprise the biocidal fibers or particles or a blend of the fibers or particles with synthetic or natural materials. For example, the filters may be a woven or non-woven fabric of a yarn blended with thermoplastic, thermosetting or natural materials. A blend with about 30 to 50% other fibers or particles is satisfactory in most cases.

Examples of the other materials that may be used as filler or reinforcement include carbonaceous or carbon fibers, cotton, wool, polyester, polyolefin, nylon, rayon, asbestos, glass fibers, fibers of silica, silica alumina, potassium titanate, silicon carbide, silicon nitride, silicon oxide, boron nitride, boron, acrylic fibers, tetrafluoroethylene fibers, polyamide fibers, vinyl fibers, protein fibers, ceramic fibers such as aluminum silicate, and oxide fibers such as boron oxide, thoria and zirconia.

Once the fibers or fibers assemblies are produced they can be used to produce various filter structures in substantially any fabricate form. For example, the filter element may be in the form of a sheet having a thickness of from 6 to 12 mm thickness, or a three-dimensionally shaped article.

Many combinations and structures are possible in this invention. The compositions prepared for a specific application will depend on the mechanical properties desired by the end-user.

The following examples illustrate certain embodiments of the invention, but the invention is not limited to the particular embodiments are illustrated.

All percentages herein being by weight unless otherwise indicated.

EXAMPLE 1

A. Preparation of Biocidal Fiber from Melt Spun Ethylene/Acrylic Acid Copolymer:

An ethylene/acrylic acid copolymer (melt index of 300 and acrylic acid content of 20 wt. %) was melt spun at 147° C. on fiber spinning equipment used for polyethylene spinning (spinnerette with 34 holes of 600 microns diameter). The copolymer was spun into a continuous filament and hauled off onto spools during spinning. Filament of 26–28 micron diameter was spun.

A six gram sample of the filament was chopped to 6 mm. length mechanically. The chopped fiber was placed in a stirred beaker containing an excess of 0.5 N NaOH solution. The mixture was digested for 5 hours at 55° C. to convert the fiber to a microporous, wettable hydrogel fiber of ethylene-sodium acrylate. The solution was cooled. The caustic was drained and the fiber was washed with water to remove excess caustic.

The swollen fiber was diluted in water to form a slurry and poured into a 100 ml. burette and the excess water drained. A 500 ml. solution of 5.0 wt. % of dimethyldidecylammonium chloride was slowly recirculated through the fibrous bed continuously at a flow rate of thirty bed volumes per hour flow rate using a masterflex variable speed peristaltic pump. After a six hour exposure time, distilled water was purged through the column to clean the fibers thoroughly (1.5 liters of purge water). The fibers were removed from the burette and air dried. A nitrogen analysis showed the new product to have 1.03 wt. % nitrogen (corresponding to 26.5 wt. % of dimethyldidecylammonium acrylate, about a 34% conversion of the carboxylate groups to the biocidal quat form). Sodium analysis of the fiber (before and after treatment) showed that the residual sodium was reduced from 4.2 wt. % to 21 ppm. (99.95% replacement of available sodium with the dimethyldidecylammonium cation).

Samples of the melt spun ethylene-acrylic acid dimethyldidecylammonium acrylate were submitted to a Biolab for testing. Four types of microorganisms were tested (petri dish tests containing agar and a few fibers were inoculated with microorganisms to determine if the organisms would form colonies or die). Complete kill was observed for the four organisms tested (mucor miehei, candida albicans, pircicula riacryzac, aspergillis niger). The fiber definitely exhibited biocidal properties and the dimethyldidecylammonium acrylate groups were linked to the biocidal properties. The fibers could be placed in a cartridge for use in the reservoir of a lavatory.

B. A one gram sample of the melt spun ethylene-acrylic acid dimethyldidecylammonium acrylate polymer was placed in a bottle containing an excess 5.0 wt. % salt (NaCl) solution and the fiber exposed for several days. Nitrogen analysis of the salt solution showed the nitrogen analysis to be undetectable (>0.5 ppm nitrogen detected) and the residual fiber still contained 1.03 wt. % nitrogen. The biocidal hydrogel fiber was stable to the salt solution, indicating that the biocidal quaternary compound exhibited a very strong affinity for the polymer fiber compared to sodium ions. The dimethyldidecylammonium acrylate groups were likewise found to be stable to 5 wt. % urea solutions.

EXAMPLE 2

A. Preparation of Biocidal Fiber from Melt Blown Ethylene Acrylic Acid:

An ethylene/acrylic acid copolymer (melt index of 300 and acrylic acid (A.A.) content of 20 wt. %) was melt blown at 147 degrees Celsius and blown in high speed air into a mass. The diameter was 30 microns for this melt blown filament.

A six gram sample of the melt blown filament was chopped to 5 mm. lengths mechanically and the melt blown fibers digested in 0.5 N caustic solution at 55° C. for 5 hours. The procedures of Example No. 1 were used to produce a white, fiber containing 1.06 wt. % nitrogen. This corresponded to a about 34% conversion of the carboxylic acid groups, but represented a complete interchange of the available sodium groups for dimethyldidecylammonium cation groups. The fiber obtained would correspond to a composition containing 27.3 wt. % dimethyldidecylammonium acrylate.

B. Biocidal testing of the melt blown fibers showed complete kill of the four organisms tested (mucor miehei, candida albicans, pircucula riacryzac, aspergillis niger). Biocidal properties were indistinguishable from the melt spun fiber of Example No. 1.

The dimethyldidecylammonium acrylate groups were found to be stable to 5 wt. % sodium chloride (aqueous solution) and 5 wt. % urea. The fiber may be blended with other synthetic fibers and used as a filter for an air conditioning system.

EXAMPLE 3

A. Preparation of Biocidal Fiber from Hammermill Ground Fiber:

An ethylene-acrylic acid copolymer (300 melt index/20 wt. % AA) was extruded at 198° F. into strand and chopped into granules.

Chopped granules were placed in a digestion bath containing 2 wt. % caustic heated to 55° C. and allowed to digest for 5 hours. The granules were removed and thoroughly washed with water and placed into a hammermill fitted with a 20 mesh screen. The granules were beat to a fine fiber which was 20 mesh and finer. The beat fiber was diluted to a slurry and pumped continuously onto a 40 mesh screen and a 100 mesh screen placed beneath collected a second sample.

A 12.0 gram portion of the 40 mesh screened fiber was placed in a 100 ml. burette and rinsed thoroughly with water by pumping 2 liters of purge water slowly through the fibrous bed. A white, fibrous bed of about 11 inches bed depth was obtained.

A 500 ml. portion of solution containing 5.0 wt. % of dimethyldidecylammonium chloride was recirculated through the bed for six hours at a flow rate of 30 bed volumes per hour.

After the six hour reaction period, the bed was drained and thoroughly washed with 3 liters of deionized water and then further rinsed by recycling four hours with water to remove any trace chemicals. The fibrous product was removed from the column and air dried.

Nitrogen analysis of the sample showed 0.49 wt. % nitrogen (corresponding to about 15% conversion of carboxylic acid functionality).

B. The hammermill ground biocidal fiber was tested for biocidal activity and it was observed that addition of small amounts of the fiber to agar gave complete kill to the four test organisms of Examples No. 1 and 2.

EXAMPLE 4

A. Preparation of Hammermill Ground Biocidal Fiber:

A dry 120 gram sample of 20–40 mesh hammermill ground, porous fiber was hydrated in water and placed in a one liter column. Three volumes of dimethyldidecylammonium chloride were pumped through the column and discarded. A fresh solution of 2600 ml. of 7.7 wt. % dimethyldidecylammonium chloride solution was recirculated through the bed for 12 hours continuously to drive the ion exchange reaction to completion. The bed was drained and deionized water pumped through the bed until the fiber was purged clean of reactants. The sodium content of the parent was 4.8 wt. % and only about 20 ppm in the biocidal derivative. The nitrogen content of the parent fiber was undetectable (<0.5 ppm) but was 1.9 wt. % on the biocidal fiber derivative. This corresponds to an almost quantitative conversion of the fiber with the quaternary ammonium compound.

It was noted that the biocide does not have to elute into the environment in measurable amounts to produce biocidal effects. The polymer is biocidal itself and appears to kill microorganisms on contact.

B. To test the stability of the biocide in hard water a 100 ml. burette with a bed of about 20 inches of the 20–40 mesh hammermill ground fiber was prepared and a solution containing 400 ppm of Ca ions pumped through the bed continuously at a flow rate of 20 ml. per minute (with samples taken at 5 minute intervals with the test continued for 2 hours) with nitrogen undetected in any eluted sample and calcium ions remained at 400 ppm during the duration of the test. Trace sodium was 5–10 ppm initially but was quickly eluted by the excess calcium. The biocidal quaternary acrylate was very stable to the calcium indication a very high (unexpectedly high stability) for the biocidal quaternary acrylate groups.

EXAMPLE 5

The bottom portion of a nylon stocking was removed for use as a pouch. About 40 grams of the hammermill ground fiber of Example No. 4 (1.9 wt. % nitrogen fixed in the polymer as dimethyldidecylammonium acrylate) was placed in the bottom of the pouch and the pouch tied off and a stainless steel hanger made so that the pouch remained below the water surface in the toilet reservoir and drained then refilled with fresh water each time the toilet is flushed.

On use of the pouch, the odor level diminished to an insignificant level and remained at an insignificant odor level during the duration of the test 150 days of continuous use. Samples of the used fiber were removed at 30 day intervals for analysis of residual nitrogen and metals. The following analysis was obtained from for the first 90 day test period.

| Days of Use* | Nitrogen (wt. %) | ppm of Metals in Fiber, ppm | | | |
|---|---|---|---|---|---|
| | | $Fe^{+++}$ | $Ca^{++}$ | $Mg^{++}$ | $Na^+$ |
| 0 | 1.90 | 21 | 26 | 4.9 | 24 |
| 30 | 1.50 | 15 | 400 | 11.0 | 23 |
| 60 | 1.47 | 25 | 290 | 93 | 91 |
| 120 | 1.33 | 43 | 330 | 94 | 46 |

The city water used contains 800–1100 ppm of total dissolved solids with about 150–250 ppm of calcium and about 30–60 ppm magnesium with a methyl orange test rating of about 750 (mostly bicarbonate).

The nitrogen loss is representative of biocidal activity and samples of and fibers of 0.45 wt. % fixed nitrogen tested to give 100% kill for test organisms then the 1.33% represents an active biocidal fiber after 4 months of use. An expected service life at a loss rate of 0.006% nitrogen per day (an average loss of about 22 milligrams of dimethyldidecylammonium cation per day) might be in excess of 300 days. The biocide is proven to be strongly active at the 0.5 wt. % level.

EXAMPLE 6

The procedures of Example 3 were repeated with the change that mixed biocidal agents with biocidal kill for a wide spectrum of fungi, algae, and bacteria was substituted for the dimethyldidecylammonium chloride solution. Nitrogen analysis for the resulting biocidal fiber was 1.4 wt. % indicating a high wt. % content of mixed dimethyldifattyammonium acrylates. The exact composition (mixed quat acrylates) was not determined. It was clearly shown that the ion exchange reaction is not restricted to substitution of sodium with dimethyldidecylammonium ions. The interchange chemistry is generally applicable to a range of dimethyldifattyammonium ions. The four test organisms were killed by the hydrogel fiber containing biocide. The modified polymer itself is biocidal and does not have to elute the biocide into the environment in any measurable amount to produce biocidal effects.

EXAMPLE 7

A plexiglass axial flow cartridge 9¼ inches long by 1 1/5 inches in diameter was loaded axially with 30–50 micron diameter melt spun fibers (continuous filaments stretched axially the length of the cartridge, with a polymer composition of ethylene-acrylic acid copolymer of 300 melt index and 20 wt. % acrylic acid content). A 0.5 N caustic solution was recirculated at 65° C. for two hours to convert the fiber to a microporous hydrogel, ion exchange form. Excess caustic was purged out with water.

An excess of a solution containing 20 wt. % of dimethyldidecylammonium chloride was recirculated overnight through the axial flow cartridge with flow axial along the fiber length. The biocidal cartridges were purged thoroughly with water until nitrogen could not be detected in the purge water ($<1$ ppm nitrogen). An additional 5 gallons of deionized water was purged through the system to insure soluble biocide removal. The point of testing was strictly to determine utility of the cartridge as a kill-on-contact device for bacteria.

The cartridge was placed in a system to clean up river water. The river water was passed through a 100 micron filter then through a mixed resin bed to demineralize the water and then sampled periodically before and after the biocidal cartridge. The inlet water contained 20,000 bacteria/ml. (called colony forming units) with sampling over an 11 hour run at 30 intervals and a total elution of 18 gallons of treated water (1.6 gallons/hour flow rate). The kill level was in excess of 98.5%.

EXAMPLE 8

A. Preparation of Biocidal Fibrous Nonwoven Mat

A 15 gm. portion of 70 micron diameter melt spun fiber of ethylene-acrylic acid (300 melt index, 20 wt. % acrylic acid) was chopped into 6 mm. fiber lengths and digested in hot aqueous caustic (0.5 N NaOH, 2 hours) to produce microporosity, wettability and ion exchange properties. The fiber was allowed to soak in the caustic at room temperature then drained and thoroughly washed to remove residual caustic. A sample of the fiber was tested for capacity and found to absorb 5.2 wt. % copper (1.6 meq/gram of dry fiber). A solution containing 10 wt. % dimethyldidecylammonium chloride was recirculated through a fibrous mat of the ion exchange fiber described above for 2 hours and then residual chemicals washed out with deionized water. The sample was air dried and desiccated, then analyzed for nitrogen (1.5 wt. % nitrogen was obtained which corresponded to about 79% conversion to the dimethyldidecylammonium acrylate form, or about 35 wt. % of dimethyldidecylammonium acrylate in the fibrous mat). The mat can be utilized to destroy and inhibit microbiotic activity in water. If desired other biocides may be used in lieu of or together with dimethyldidecylammonium chloride.

EXAMPLE 9

A 2 gram portion of the caustic swelled fiber similar to that used in Example 8 above was treated with a solution containing 1000 ppm of aluminum (aluminum sulfate solution used) and excess aluminum was washed out with deionized water. The fiber was then treated overnight with a solution of 10 wt. % of dimethyldidecylammonium chloride which was recirculated through the fiber in a burette. Analysis showed the fiber to contain 0.34 wt. % aluminum and 1.3 wt. % nitrogen. The overall conversion to % or about 30 wt. % dimethyldidecylammonium acrylate with about 3.4 wt. % aluminum acrylate present in the polymer.

EXAMPLE 10

A 0.1" diameter strand of ethylene/acrylic acid copolymer (20% acrylic acid, 300 8/10 min. melt flow rate) was cold-drawn to 15-20% orientation and then swollen 4 hours in 0.61 N NaOH at 60°-65° C. The filament was pressed into a steel roller which caused it to fibrillate into a "tape" of microfilaments bundles and then was pulped into an aqueous slurry (0.5% solids) using a Waring blender for a few seconds. The so-formed pulp fibers were, typically ribbon-like strands of about 5 micron thickness, about 35 micron width, and about 3/16" to ¼" length. The blades of the Waring blender were intentionally installed backward in order to "beat" the polymer into pulp rather than use the sharp edge of the blades which would cut the fibers. Cutting the fibers would result in fewer fibrils and more fines.

Some of the pulp fibers were washed and vacuum-drawn as a felt on a 100-mesh stainless steel screen, a solution containing 20 wt. % of dimethyldidecylammonium chloride was recirculated overnight through the felt to form an amide-modified filter pad.

Although the invention has been described with respect to specific embodiments, it will be understood that other variations may be made without departing from the scope of the invention as defined in the following claims.

What is claimed is:

1. A water insoluble biocidal filter for use in fluid systems comprising a water insoluble thermoplastic hydrogel copolymer consisting of an alpha olefin and an alpha, beta-ethylenically unsaturated carboxylic acid, said copolymer having at least one cationic biocidal agent ionically bonded to said copolymer.

2. The biocidal filter of claim 1 wherein said copolymer is in fiber or particle form.

3. The biocidal filter of claim 1 wherein said copolymer is microporous.

4. The biocidal filter of claim 1 wherein said copolymer comprises a blend of thermoplastic materials.

5. The biocidal filter of claim 1 wherein said biocidal agent is a quaternary ammonium salt selected from the group consisting of alkylbenzyldimethylammonium halide, wherein said alkyl group contains 12 to 18 carbon atoms, and dimethyldialkylammonium halide, wherein said alkyl group contains 8-10 carbon atoms.

6. The biocidal filter of claim 5 wherein said quaternary ammonium salt is dimethyldidecylammonium chloride.

7. The biocidal filter of claim 1 wherein said monocarboxylic acid component comprises 0.2 to 25 mol percent of said copolymer.

8. The biocidal filter of claim 1 wherein said copolymer comprises an alpha-olefin of the general formula $R-CH=CH_2$, wherein R is selected from the group consisting of hydrogen and an alkyl group having from 1 to 8 carbon atoms.

9. The biocidal filter of claim 1 wherein the alpha, beta-ethylenically unsaturated acid is selected from the group consisting of acrylic acid, methacrylic acid, ethacrylic acid, maleic acid and fumaric acid.

10. The biocidal filter of claim 1 wherein said copolymer is the reaction product of ethylene and maleic anhydide.

11. The biocidal filter of claim 1 wherein said alpha-olefin is ethylene.

12. The biocidal filter of claim 1 wherein said copolymer is derived from an ionomer.

13. The biocidal filter of claim 1 comprising a blend of the biocidal fibers with non-biocidal fibers.

14. In an apparatus for the passage of a fluid having a filter element, the improvement which comprises said filter element being composed of fibers and/or particles of a water insoluble thermoplastic hydrogel copolymer consisting of an alpha olefin and an alpha, beta-ethylenically unsaturated carboxylic acid, said copolymer having at least one cationic biocidal agent ionically bonded to said copolymer.

15. A method for the treatment of a fluid system so as to destroy or inhibit microorganisms comprising passing said fluid through a filter comprising fibers and/or particles of a water soluble thermoplastic hydrogel copolymer consisting of an alpha olefin and an alpha, beta-ethylenically unsaturated carboxylic acid, said copolymer having at least one cationic biocidal agent ionically bonded to said copolymer.

16. The method of claim 15 wherein said fluid system comprises water.

17. The method of claim 15 wherein said fluid system comprises air.

18. The method of claim 15 wherein said microorganism comprises at least one type of bacteria.

19. The method of claim 15 wherein said microorganism comprises at least one type of fungus or yeast.

20. The method of claim 15 wherein said filter comprises fibers.

21. The method of claim 15 wherein said filter comprises particles.

22. A permeable biocidal material useful as a biocidal filter or barrier structure, said material comprising:
a water insoluble thermoplastic hydrogel copolymer consisting of an alpha-olefin and alpha, beta-ethylenically unsaturated carboxylic acid,
said copolymer having at least one cationic biocidal agent ionically bonded to said copolymer.

23. The material of claim 22, wherein the copolymer comprises a copolymer of ethylene and acrylic acid and the biocidal agent comprises at least one of the group consisting of:
alkylbenzyldimethylammonium halide, in which the said alkyl group contains 12 to 18 carbon atoms, and
dimethyl dialkylammonium halide, in which the said alkyl group contains 8 to 10 carbon atoms.

* * * * *